United States Patent [19]

Takahashi et al.

[11] Patent Number: 4,877,733

[45] Date of Patent: Oct. 31, 1989

[54] GLUCOSE DEHYDROGENASE AND ITS PRODUCTION

[75] Inventors: Mamoru Takahashi; Shigeyuki Imamura; Masaki Takada, all of Shizuoka, Japan

[73] Assignee: Toyo Jozo Kabushiki Kaisha, Shizuoka, Japan

[21] Appl. No.: 42,655

[22] Filed: Apr. 28, 1987

[30] Foreign Application Priority Data

May 2, 1986 [JP] Japan .................................. 61-101183
Mar. 16, 1987 [JP] Japan .................................. 62-58874

[51] Int. Cl.$^4$ ................................................ C12N 9/04
[52] U.S. Cl. ...................................... 435/190; 435/189; 435/911; 435/254
[58] Field of Search ................. 435/189, 190, 911, 254

[56] References Cited

U.S. PATENT DOCUMENTS 4,397,952  8/1983  Von Hoerschelmann et al. .......................................... 435/190

Primary Examiner—Robert A. Wax
Assistant Examiner—Mary E. Pratt
Attorney, Agent, or Firm—Young & Thompson

[57] ABSTRACT

Glucose dehydrogenase having the following biochemial properties:
 (a) enzymatic action: catalyzes a reaction which generates glucono-δ-lactone and reduced NADP from glucose and NADP;
 (b) substrate specificity: has substrate specificity on glucose and no substrate specificity on 2-deoxyglucose;
 (c) optimum pH: pH 6–8,
(d) optimum temperature: approximately 55° C.,
 (e) pH-stability: stable at pH 6.0–7.5,
 (f) molecular weight: $11 \times 10^4 \pm 11000$,
 (g) Km-value: $2.6 \times 10^{-3} \pm 2.6 \times 10^{-4}$M(glucose) $4.2 \times 10^{-6}$ $^{35}$ $4.2 \times 10^{-7}$M(NADP) and
 (h) isoelectric point: $4.9 \pm 0.5$, comprises culturing a glucose dehydrogenase-producing microorganism *Cryptococcus uniguttulatus* Y 0033 FERM P-8709, now FERM BP-1352 in a nutrient medium and isolating glucose dehydrogenase thus produced from the cultured medium.

3 Claims, 2 Drawing Sheets

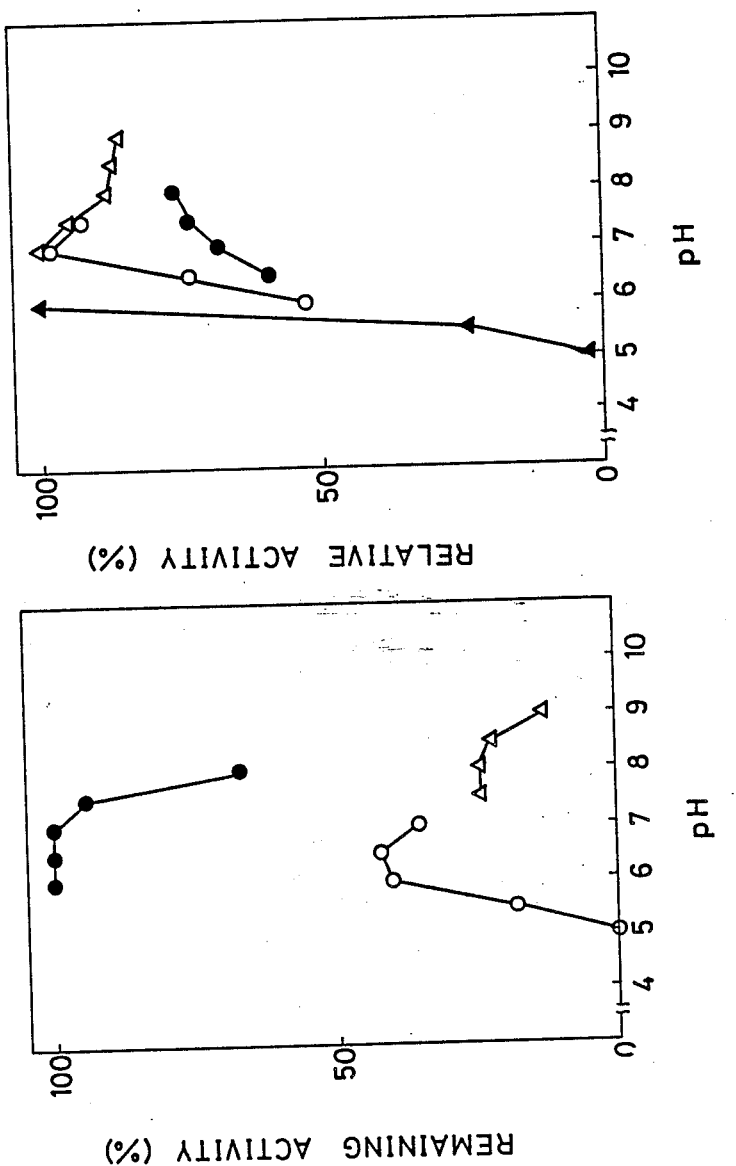

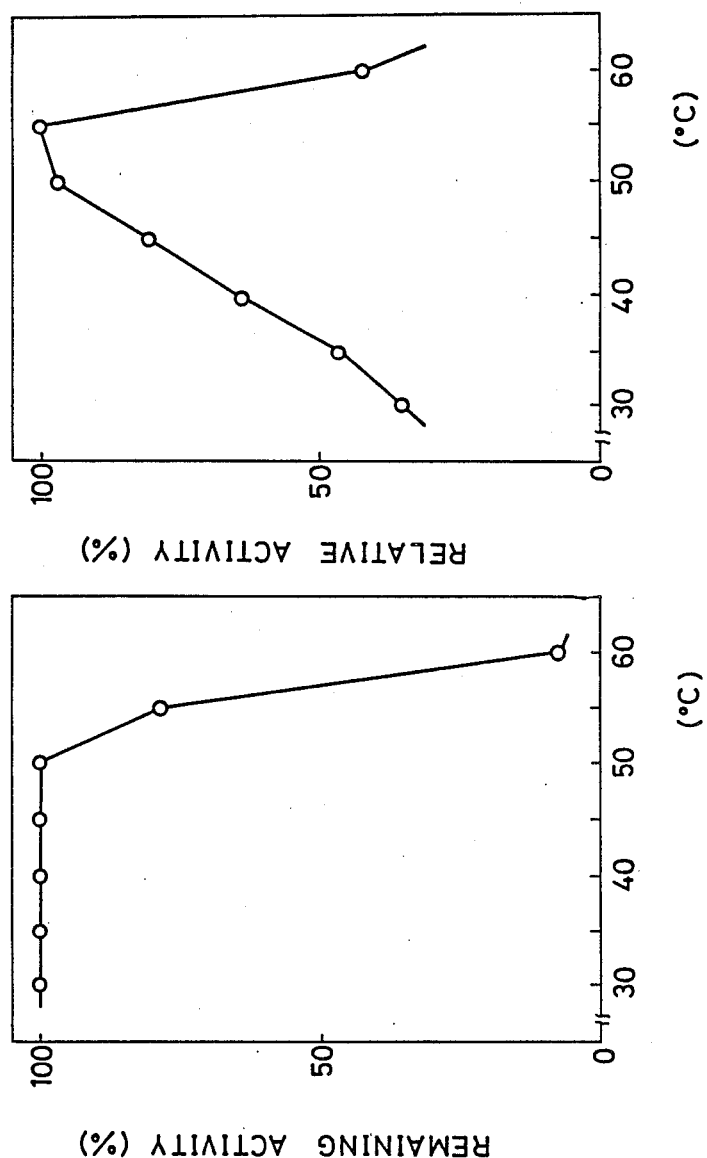

GLUCOSE DEHYDROGENASE AND ITS PRODUCTION

This invention relates to glucose dehydrogenase which has high reactivity and substrate specificity on glucose, and to a process for the production thereof.

BACKGROUND OF THE INVENTION

Glucose dehydrogenase is an enzyme which catalyzes the reaction:

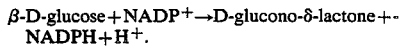

$$\beta\text{-D-glucose} + NADP^+ \rightarrow \text{D-glucono-}\delta\text{-lactone} + NADPH + H^+.$$

Recently, in the field of clinical chemistry, the quantitative determination of glucose in a specimen using the above enzymatic reaction has been effected, and the demand for glucose dehydrogenase is increasing.

Heretofore, a process for the production of glucose dehydrogenase by microorganisms, for example *Bacillus megaterium* (Jap. Pat. Unexam. Publ. No. 58-201985), *Bacillus cereus* (Jap. Pat. Unexam. Publ. No. 57-16693) and Acetobacter, Acinetobacter, Gluconobacter or Pseudomonas (Jap. Pat. Unexam. Publ. No. 59-25700) has been known. However, these processes have a number of disadvantages. For example, the substrate specificity of glucose dehydrogenase from Gluconobacter is so broad as to exhibit the value 227 on 2-deoxy-glucose and 95 on mannosamine as compared with 100 on glucose. (Enzyme Handbook, page 43, Asakura Publ. Co., Tokyo, 1983.)

OBJECTS OF THE INVENTION

An object of the present invention is to provide novel glucose dehydrogenase having high reactivity and substrate specificity on glucose.

Another object of the present invention is to provide a process for the production of glucose dehydrogenase.

SUMMARY OF THE INVENTION

The present invention provides glucose dehydrogenase having the following biochemical properties:
(a) Enzymatic action: catalyzes a reaction which generates glucono-δ-lactone and reduced NADP from glucose and NADP; and
(b) Substrate specificity: has substrate specificity on glucose and no substrate specificity on 2-deoxy-glucose.

The present invention also relates to a process for the production of glucose dehydrogenase, which comprises culturing a glucose dehydrogenase-producing microorganism belonging to genus Cryptococcus in a nutrient medium and isolating glucose dehydrogenase thus produced from the said cultured medium.

BRIEF DESCRIPTION OF THE DRAWINGS

In the accompanying drawings:
FIG. 1 is a graph of the pH stability of the glucose dehydrogenase according to the present invention;
FIG. 2 is a graph of the optimum pH thereof;
FIG. 3 is a graph of the heat stability thereof; and
FIG. 4 is a graph of the optimum temperature thereof.

DETAILED DESCRIPTION OF THE INVENTION

The glucose dehydrogenase-producing microorganism can be a microorganism belonging to genus Cryptococcus, and is preferably *Cryptococcus uniguttulatus* Y 0033 FERM P-8709, now Ferm BP-1352.

The taxonomical properties of the above strain are illustrated as follows:
1. Growth on various media;
(1) YM liquid medium:
Upon 3 days culture at 25° C., the vegetative hyphae are spherical to elliptical, 2–5×4–5 μm. Grows by multipolar budding. Forms a white powdery precipitate. Forms in a ring-shape from fifth day of culture.
(2) YM agar medium:
Round colony with entire edge. Convex shaped bulging. Smooth surface. Glistening. Butyrous property. Color white.
(3) Slide culture on potato extract agar medium:
No formation of pseudomycelium.
2. Formation of ascospore: —
3. Formation of ballistospore: —
4. Physiological properties:
(1) Optimum growth condition: pH 5–9, temperature 24°–30° C.
(2) Growth range: pH 4.5–11.5, temperature 19°–33° C.
(3) Assimilation of nitrate: —
(4) Degradation of lipid: —
(5) Degradation of urea: +
(6) Liquefaction of gelatin: —
(7) Osmophilic or osmotolerant: —
(8) Formation of carotenoid: —
(9) Formation of organic acid: —
(10) Formation of starch-like substance: —
(11) Growth on vitamin deficient medium: +W
5. Utilization of carbon sources:
Fermentative:
   D-glucose —
   D-glactose —
   maltose —
   sucrose —
   lactose —
   raffinose —
Assimilability:
   D-arabinose +S (slowly)
   L-arabinose +
   D-ribose +
   D-xylose +W (weakly)
   D-glucose +
   D-mannose —
   D-galactose —
   D-rhamnose +
   D-fructose —
   L-sorbose —
   maltose +
   sucrose +
   lactose —
   melibiose —
   cellobiose —
   trehalose +
   raffinose +
   melezitose +
   α-methyl-D-gluoside +
   arbutin +
   dextrin —
   soluble starch +W (weakly)
   inulin +W (weakly)
   ethanol ±
   adonitol ±
   erythritol — inositol +
D-mannitol +
D-sorbitol +
dulsitol −
D-gluconate −
glycerol −
2-keto-D-gluconate +
DL-lactate −
succinate −
citrate −

A microorganism hereinabove was isolated from a soil sample collected from a pigpen at Ohito-cho, Tagatagun, Shizuoka-ken, Japan and is a yeast. The said microorganisms grow by multipolar budding and do not form ascospores, ballistspores and pseudohyphae. It assimilates inositol. These characteristics show the microorganism to belong to the genus Cryptococcus. According to the physiological properties of the present microorganism, showing a pattern of assimilation of carbon sources, no assimilation of nitrate, requirement of vitamins and no growth at 37° C., this strain is referred to as *Cryptococcus uniguttulatus* and has been designated as *Cryptococcus uniguttulatus* Y 0033. This strain has been deposited in The Fermentation Research Institute permanent culture collection and assigned No. FERM P-8709, now FERM BP-1352.

Glucose dehydrogenase of the present invention can be produced by the conventional enzyme production process using yeast culture. Yeast is inoculated into a medium and cultured under submerged aeration conditions.

Nutrient sources for the medium are conventional media for microorganism cultivation. Nutrient sources are assimilable nitrogen sources such as corn steep liquor, soybean powder, casein hydrolyzate, peptone, yeast extract and meat extract. Preferred carbon sources are assimilable carbon sources, for example disaccharides such as glucose, maltose, sucrose and lactose, and dextrin, starch, molasses or the like.

The culturing temperature can be varied depending on the growth of microorganisms and glucose dehydrogenase production, and is 25°–37° C., preferably at about 30° C. The culturing time depends on the conditions and is usually 20–50 hours. Cultivation should be terminated at the stage of maximum production of the enzyme.

Glucose dehydrogenase is isolated from the thus-obtained cultured medium. An example of the enzyme isolation is that the cultured medium is treated by filtration or centrifugation to separate mycelia and the isolated mycelia are treated by ultrasonication, supplied to a French press or subjected to mechanical disruption using glass beads, or are autolyzed with an organic solvent to obtain a crude glucose dehydrogenase solution. The crude enzyme solution is heated at 50° C. for 10–30 minutes and immediately centrifuged to separate the supernatant solution. Further purification can be achieved by ion-exchange chromatography using DEAE-cellulose, DEAE-Sephadex A-25, DEAE-Sepharose, CM-cellulose, CM-Sephadex C-25, or CM-Sepharose CL-6B, thereafter by treating with hydroxylapatite chromatography, with lyophilization if required to obtain the purified glucose dehydrogenase powder.

The following example illustrates the present invention but is not to be construed as limiting.

EXAMPLE

Production of glucose dehydrogenase by culturing *Cryptococcus uniguttulatus* Y 0033:

(i) One loopful of *Cryptococcus uniguttulatus* Y 0033 FERM P-8709, now FERM BP-1352 was inoculated into an aqueous medium (100 ml) comprising yeast extract powder 0.5%, meat extract 1.0%, glucose 1.0%, $KH_2PO_4$ 0.15%, $CaCl_2.2H_2O$ 0.033%, $MgSO_4.7H_2O$ 0.05% and NaCl 0.2% in an Erlenmeyer flask, and the mixture was shake cultured at 30° C. for 50 hours. The cultured broth was centrifuged (4500 rpm, 10 mins.) to obtain mycelia. The mycelia suspended in 10 mM phosphate buffer solution (pH 7.0, 10 ml) were disrupted using a Brown homogenizer and centrifuged (15000 rpm, 10 mins.) for removing mycelial residue to obtain the supernatant solution (10 ml, 0.6 unit/ml).

(ii) One loopful of *Cryptococcus uniguttulatus* Y 0033 FERM P-8709, now FERM BP-1352 was inoculated into an aqueous medium (100 ml) comprising yeast extract powder 0.5%, casamino acid 1.0%, sucrose 2.0%, $KH_2PO_4$ 0.15%, $CaCl_2.2H_2O$ 0.033%, $MgSO_4.7H_2O$ 0.05% and NaCl 0.2% in an Erlenmeyer flask, and the mixture was shake cultured at 30° C. for 50 hours. The cultured broth was treated in the same way as in (i) hereinabove to obtain a crude enzyme solution (10 ml, 14 units/ml).

(iii) One loopful of *Cryptococcus uniguttulatus* Y 0033 FERM P-709, now FERM BP-1352 was inoculated into an aqueous medium (100 ml) comprising yeast 0.5%, bonito extract 1.0%, maltose 1.0%, $KH_2PO_4$ 0.15%, $CaCl_2.2H_2O$ 0.033%, $MgSO_4.7H_2O$ 0.05% and NaCl 0.2% in an Erlenmeyer flask, and the mixture was shake cultured at 30° C. for 50 hours. The cultured broth was treated in the same way as in (i) hereinabove to obtain a crude enzyme solution (10 ml, 6 units/ml).

(iv) The crude enzyme solution (150 ml) obtained from a cultured broth (1050 ml) prepared in the same way as in (ii) hereinabove, was heated at 50° C. for 15 mins. and centrifuged (4500 rpm, 10 mins.) The thus-obtained supernatant solution was passed through a column (4.8×4 cm) of DEAE-Sepharose C L-6B to adsorb the enzyme and eluted with solutions of 0.1M KCl (100 ml), 0.2M KCl (100 ml) and 0.3M KCl (100 ml). Glucose dehydrogenase was eluted with 75 ml of 0.3M KCl. The enzyme solution was treated with a diaflow membrane (Amicon Co.) to desalt the same and was adsorbed on a column (4.8×1 cm) of hydroxylapatite (Sigma Chem. Co.) which was eluted with 0.1M phosphate buffer solution (pH 7.0, 50 ml), 0.2M phosphate buffer solution (pH 7.0, 50 ml) and 0.3M phosphate buffer solution (pH 7.0, 50 ml). Glucose dehydrogenase was eluted with 20 ml of 0.3M phosphate buffer solution to obtain an enzyme solution (20 ml, 23.6 units/ml).

The glucose dehydrogenase thus obtained has the following properties:

(a) Enzyme action:

Catalyzes a reaction which generates glucono-δ-lactone and reduced NADP from glucose and NADP as shown below.

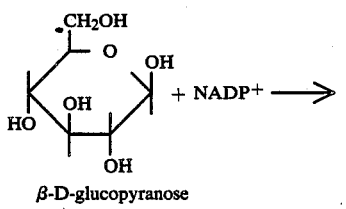

β-D-glucopyranose

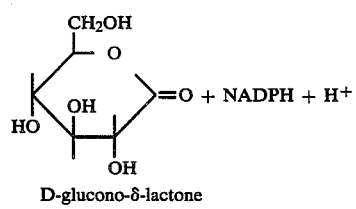

D-glucono-δ-lactone (b) pH-stability:

The remaining activity of the enzyme (1 unit/ml, 40 mM buffer solution) after heating at 53° C. for 10 mins. is shown in FIG. 1. The enzyme is stable at pH 6.0–7.0. In the figure:

— : dimethylglutarate buffer; — : phosphate buffer; — : Tris-HCl buffer. (These symbols are the same as in all figures hereinbelow, if not otherwise specifically indicated.)

(c) Optimum pH:

pH 6–8 as shown in FIG. 2. In the figure: — : acetate buffer.

(d) Heat stability:

The remaining activity of the enzyme (1 unit/ml, 40 mM phosphate buffer solution, pH 6.0) after treating at various temperatures for 10 mins. is shown in FIG. 3. The enzyme is stable up to 50° C.

(e) Optimum temperature:

Approximately 55° C. as shown in FIG. 4.

(f) Molecular weight:

$11 \times 10^4 \pm 11000$ (measured by Sephacryl S-200 superfine)

(g) Isoelectric point: pH $4.9 \pm 0.5$.

(h) Km-value: $2.6 \times 10^{-3} \pm 2.6 \times 10^{-4}$M (glucose), $4.6 \times 10^{-6} \pm 4.6 \times 10^{-7}$M (NADP), (measured in Tris-HCl buffer, pH 7.5)

(i) Effect of metallic ions and surface active agents: shown in Table 1.

(j) Substrate specificity:

Shown in Table 2 (substrate 50 mM, enzyme 0.005 U, 10 mins.)

Enzyme activity and remaining activity are measured by the following assay method:

| Assay method: | |
|---|---|
| 0.2 M Tris-HCl buffer (pH 7.5) | 0.4 ml |
| 10 mM NADP | 0.05 |
| 10% Triton X-100 | 0.01 |
| 0.5 M glucose | 0.1 |
| purified water | 0.44 |
| | 1.00 |

The above reaction mixture (1.0 ml) is preincubated at 37° C. for 2–3 mins. Enzyme solution (20 μl) is added thereto and the mixture is incubated at 37° C. for 10 mins. and the optical density at 340 nm is measured.

One unit is defined by the amount of enzyme which generates 1 μmole of reduced NADP in one minute.

TABLE 1

| | Conc. | Relative activity |
|---|---|---|
| No addition | — | 100% |
| KCl | 10 mM | 99.2 |
| NaCl | 10 | 100 |
| NH$_4$Cl | 10 | 100.8 |
| MgCl$_2$ | 10 | 102.6 |
| CaCl$_2$ | 10 | 102.3 |
| BaCl$_2$ | 1 | 98.4 |
| ZnCl$_2$ | 1 | 4.9 |
| MnCl$_2$ | 1 | 49.6 |
| NiCl$_2$ | 1 | 89.7 |
| CuCl$_2$ | 1 | 0 |
| CoCl$_2$ | 1 | 102.7 |
| HgCl$_2$ | 1 | 0 |
| AlCl$_3$ | 1 | 103.1 |
| FeCl$_3$ | 1 | 60.5 |
| Na$_2$WO$_4$ | 1 | 97.7 |
| K$_2$CrO$_4$ | 1 | 2.3 |
| EDTA | 1 | 101 |
| Nonidet P-40 | 0.1% | 236 |
| Adekatol PC-8 | 0.1 | 231 |
| Adekatol SO-120 | 0.1 | 251 |
| Tween 80 | 0.1 | 201 |
| Bridge 35 | 0.1 | 193 |
| Triton X-100 | 0.1 | 215 |
| Nikkol HCO-100 | 0.1 | 221 |

TABLE 2

| Substrate | Relative activity (%) |
|---|---|
| glucose | 100 |
| glucose-1-phosphate | 0 |
| glucose-6-phosphate | 0 |
| fructose | 0 |
| galactose | 0 |
| xylose | 19 |
| lactose | 0 |
| maltose | 0 |
| sucrose | 0 |
| 2-deoxy-glucose | trace* |
| 2-deoxy-ribose | 0 |
| cellobiose | trace* |
| glucosamine | trace* |

As illustrated hereinabove, the present invention provides a novel glucose dehydrogenase and a novel method for its production.

Comparing the present novel glucose dehydrogenase with prior known enzymes such as an enzyme derived from Bacillus cereus (Methods in Enzymology, Vol. 9, p. 109), the Km value of the enzyme of the present invention is quite low ($2.6 \times 10^{-3}$M), whereas that of the prior known enzyme is higher ($2 \times 10^{-2}$M), namely, the new enzyme is approximately ten times more active than the earlier one, which shows the superior nature of the glucose dehydrogenase of the present invention.

What is claimed is:

1. Glucose dehydrogenase having the following biochemical properties:
   (a) enzymatic action: catalyzes a reaction which generates glucono-δ-lactone and reduced NADP from glucose and NADP; and
   (b) substrate specificity: has substrate specificity on glucose and no substrate specificity on 2-deoxy-glucose.

2. A glucose dehydrogenase according to claim 1, having the following properties:
   (c) optimum pH: pH 6–8,
   (d) optimum temperature: approximately 55° C.,
   (e) pH-stability: stable at pH 6.0–7.5,
   (f) molecular weight: $11 \times 10^4 \pm 11000$, (g) Km-value: $2.6\times10^{-3}\pm2.6\times10^{-4}$M (glucose), $4.2\times10^{-6}\pm4.2\times10^{-7}$M (NADP) and (h) isoelectric point: $4.9\pm0.5$.

3. A process for the production of glucose dehydrogenase as claimed in claim 2, which comprises culturing the glucose dehydrogenase-producing microorganism *Cryptococcus uniguttulatus* Y 0033 FERM P-8709, now FERM BP-1352, in a nutrient medium and isolating glucose dehydrogenase thus produced from the cultured medium.

* * * * *